United States Patent [19]

Tobin et al.

[11] 4,006,185
[45] Feb. 1, 1977

[54] 5-SUBSTITUTED-2-FLUOROANILINES

[75] Inventors: John H. Tobin, Beacon Falls; John A. Wojtowicz, Cheshire, both of Conn.

[73] Assignee: Olin Corporation, New Haven, Conn.

[22] Filed: Dec. 20, 1974

[21] Appl. No.: 535,073

Related U.S. Application Data

[63] Continuation-in-part of Ser. No. 381,838, July 23, 1973, abandoned.

[52] U.S. Cl. .............................. 260/575; 260/578; 260/580
[51] Int. Cl.² .................. C07C 85/00; C07C 87/00
[58] Field of Search .......... 260/575, 578, 580, 581

[56] References Cited

UNITED STATES PATENTS

| | | | |
|---|---|---|---|
| 3,067,253 | 12/1962 | Dietzler et al. | 260/580 X |
| 3,194,839 | 7/1965 | Robinson et al. | 260/578 X |
| 3,310,583 | 3/1967 | de Bults et al. | 260/580 X |
| 3,558,707 | 1/1971 | Churchill et al. | 260/580 |
| 3,580,951 | 5/1971 | Churchill et al. | 260/580 |
| 3,586,719 | 6/1971 | Bil | 260/578 |
| 3,832,401 | 8/1974 | Knifton et al. | 260/575 X |

OTHER PUBLICATIONS

Fidler et al., "Aromatic Fluorine Comp'ds.," in J. Org. Chem. 26, 4014–4017, (1961).
Morrison et al., "Organic Chemistry," 3rd Ed., 1973, pp. 342, 343, *Electrophilic Aromatic Substitution*.

*Primary Examiner*—Allen B. Curtis
*Attorney, Agent, or Firm*—William A. Simons; Thomas P. O'Day; F. A. Iskander

[57] ABSTRACT

Selected 5-substituted-2-fluoroanilines, useful in preparing dyes and herbicides, are prepared by reacting a selected 3-substituted nitrobenzene with anhydrous hydrogen fluoride and a deoxygenating agent at a temperature of 0°–300° C. under a pressure of 15 to 3000 p.s.i.a. Substituents in the 3 position include hydroxyl and lower alkoxyl groups.

3 Claims, No Drawings

5-SUBSTITUTED-2-FLUOROANILINES

RELATED APPLICATIONS

The present application is a continuation in part of application Ser. NO. 381,838, filed July 23, 1973, now abandoned.

BACKGROUND

1. Field of Invention

This invention relates to a novel group of fluoroanilines, namely, selected 5-substituted-2-fluoroanilines and to a method for preparing these compounds by deoxygenating and hydrofluorinating a selected 3-substituted nitrobenzene.

2. Prior Art

The prior art discloses that deoxygenation and hydrofluorination of nitrobenzenes with an open para-position produces para-fluoroanilines. U.S. Pat. No. 3,558,707 discloses a process for producing such para-fluorinated anilines by heating a corresponding nitrobenzene with anhydrous hydrogen fluoride and a deoxygenating agent selected from the group consisting of elemental phosphorus, elemental sulfur, phosphorus trihalides, sulfur halides in which sulfur has a valence lower than 6, aryl phosphorus halides, aryl sulphenyl halides and triaryl phosphines at a temperature of 0° to 230° C. under a pressure of 15–1500 p.s.i.a. U.S. Pat. No. 3,580,951 discloses a process for preparing para-fluoroanilines utilizing a similar procedure wherein the reaction is conducted in an atmosphere containing a substantial portion of carbon monoxide. U.S. Pat. No. 3,639,482 discloses still another process for producing para-fluoroanilines wherein a nitrobenzene and anhydrous hydrogen fluoride are heated in an atmosphere of carbon monoxide in the presence of a noble metal catalyst. The preparation of parafluoroanilines by catalytic hydrogenation of nitrobenzene in anhydrous hydrogen fluoride is also disclosed and claimed in U.S. Pat. No. 2,884,458.

One skilled in the art would expect that reacting a 3-substituted nitrobenzene having an open para-position with anhydrous hydrogen fluoride and a deoxygenating agent would produce a corresponding para-fluoroaniline. It has now been discovered, however, that when a nitrobenzene substituted in the 3 position with a hydroxyl or lower alkoxyl group is reacted at elevated temperature and pressure with anhydrous hydrogen fluoride and deoxygenating agent, that fluorine substitution occurs, in the position para to the hydroxyl or alkoxyl substituent rather than in the position para to the resulting amine group as one skilled in the art would expect.

Fluoroanilines are well-known to be useful intermediates in the preparation of dyes, herbicides and pesticides and in the preparation of various other useful compounds, and the present fluoroanilines share the wide utility of this group of compounds.

In particular, the present fluroanilines are useful in the preparation of p-fluorophenols and ester, acid and ether derivatives thereof. For example, 5-hydroxy-2-fluoroaniline is converted to 4-fluorophenoxyacetic acid or esters thereof by first reacting it by known means with $NaNO_2$, HCl and $NaBF_4$ to form a corresponding diazonium fluoroborate then deaminating by refluxing in the presence of zinc and ethanol. The p-fluorophenol thus formed is then refluxed with chloroacetic acid and pyridine in the presence of benzene to form 4-fluorophenoxyacetic acid which has been reported to be effective in the control of weeds. See B. R. Andersen, et al., WEEDS, Vol. 1, No. 6 (1952). Similarly p-fluorophenol is reacted with dodecyl alcohol by known means to form 4-fluorophenyldodecyl ether, reported to be an active herbicide. See S. R. McLane et al., WEEDS, Vol. II, No. 4 (1953). The present compounds are also readily converted by known means to herbicidal nitriles such as the 4-fluorophenoxyacetonitrile disclosed in the U.S. Pat. No. 3,467,692.

These compounds are also useful intermediates for preparation of dyes. For example, 5-methoxy-2-fluoroaniline is reacted at 0° C. with $NaNO_2$ and HCl to form the corresponding diazonium chloride. The diazonium chloride is then coupled at room temperature with Naphthol A.S. to form a color fast dye having an orange to red color. See Inukai, et al., *J. Chem. Soc. Japan, Ind. Chem Section* 58, 592 (1955).

SUMMARY OF THE INVENTION

The present invention provides 5-substituted-2-fluoroanilines and a method for preparing these compounds which comprises reacting a substituted nitrobenzene having the formula:

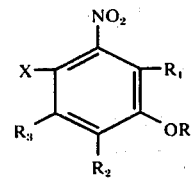

wherein X is hydrogen or halogen selected from the group consisting of chlorine, bromine, and iodine, wherein R is selected from the group consisting of hydrogen and alkyl, preferably lower alkyl having 1–4 carbon atoms, and wherein $R_1$, $R_2$, and $R_3$ are each independently selected from the group consisting of hydrogen, halogen and alkyl, preferably lower alkyl having 1–4 carbon atoms, with anhydrous hydrogen fluoride and a deoxygenating agent at a temperature of 0°–300° C. under a pressure of 15–3000 p.s.i.a. to form a corresponding 5-substituted-2-fluoroaniline.

DESCRIPTION OF THE INVENTION

Suitable nitrobenzenes are nitrobenzenes or substituted nitrobenzenes wherein the ring hydrogen in the 3 position is substituted with a member selected from the group consisting of hydroxyl and alkoxyl, preferably lower alkoxyl. Examples of suitable starting materials and principal products formed by the process of the invention include, but are not limited to the following:

| Starting Material | Product |
| --- | --- |
| 3-hydroxynitrobenzene | 5-hydroxy-2-fluoroaniline |
| 3-methoxynitrobenzene | 5-methoxy-2-fluoroaniline |
| 3-ethoxynitrobenzene | 5-ethoxy-2-fluoroaniline |
| 3-propoxynitrobenzene | 5-propoxy-2-fluoroaniline |
| 3-butoxynitrobenzene | 5-butoxy-2-fluoroaniline |

The resulting compounds are 5-substituted-2-fluoroanilines having the formula:

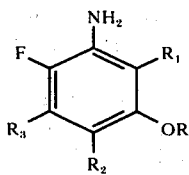

wherein R is selected from the group consisting of hydrogen or alkyl preferably lower alkyl having 1–4 carbon atoms.

As shown above various substituents may also be present on the nitrobenzene ring at positions other than the 3 position without interfering with the substitution produced in accordance with the present invention. Thus $R_1$, $R_2$, and $R_3$ may be independently selected from the group consisting of hydrogen, halogen, preferably chlorine or bromine, and alkyl, preferably lower alkyl having 1–4 carbons.

Suitable the deoxygenating agents comprise a wide range of phosphorus compounds and analogous sulfur compounds including red or yellow elemental phosphorus, elemental sulfur in any of its allotropic forms, phosphorus and sulfur halides including fluorides, chlorides, bromides and iodides of trivalent phosphorus and of sulfur lower in valence than 6. Suitable examples include $PF_3$, $PCl_3$, $S_2Cl_2$, $SCl_2$, $SCl_4$, and $S_2Br_2$. Aryl phosphorus halides, aryl sulphenyl halides and triaryl phosphines may also be used. For example, diphenyl phosphorus chloride, di-p-tolyl phosphorus chloride and benzene sulphenyl chloride, triphenylphosphine, tri-o-tolyl phosphine, tri-p-tolyl phosphine and tri-p-bromophenylphosphine. Mixtures of these deoxygenating agents are also suitable.

In the process of this invention it is believed that the deoxygenating agent acts as an oxygen acceptor to form oxidation products; for example $POCl_3$, $SOCl_2$ and triphenyl phosphine oxide. These by-products are easily separated from the product fluroanilines by means which are well known in the art.

The various deoxygenating agents vary in activity. For example, benzene sulphenyl chloride reacts even at atmospheric pressure and at 0° C. Higher temperatures, however, are preferable for most deoxygenating agents in order to obtain decreased reaction times. For example, the reaction utilizing elemental phosphorus at 150° C. proceeds to completion in about 6 hours. A much longer time would be required if the reaction were conducted at a lower temperature, for example, 50° C. Suitably, therefore, a temperature in the range of 0°–300° C, advantageously 50°–300° C, and preferably 100°–300° C may thus be utilized. If the temperature is increased within this range, reaction times will be correspondingly shortened. In general, however, reaction times will vary from about 1 to about 10 hours.

The anhydrous hydrogen fluoride utilized in the reaction supplies hydrogen for conversion of the nitro groups to $NH_2$. It also supplies fluorine for substitution of the ring. Pressures attained in the reaction are generally autogenous but higher pressures may be utilized if desired.

The molar ratio of deoxygenating agent to the starting substituted nitrobenzene is at least 0.3 to 1. In the case of elemental phosphorus, this corresponds to 0.3 gram-atoms per mole of substituted nitrobenzene. Preferably the molar ratio is at least 0.5 to 1 and ratios up to about 5 to 1 may be used if desired. Utilizing ratios below 0.3 to 1 causes yields to suffer whereas ratios in excess of 5 to 1 appear to be unnecessary.

The minimum stoichiometric molar ratio of hydrogen fluoride to substituted nitrobenzene is 1 to 1. If a lower molar ratio is utilized, yields will suffer. It is preferable that the molar ratio of hydrogen fluoride to substituted nitrobenzene be at least 1 to 1 and molar ratios up to 50 to 1 are suitable. Preferably molar ratios in the range of 10 to 1 to 40 to 1 are used. The reaction may be run in any suitable manner. For example, it may be run in closed batch reactor as shown in the accompanying examples or in a continuous co-current or countercurrent type reactor maintained at a suitable temperature and pressure.

Upon completion of the reaction, the product may be isolated in any convenient manner, for example, excess gases are allowed to evaporate or are distilled off. Water is added to the reaction product precipitating oxidation product and unconverted deoxygenating agent. The insolubles are filtered, the aqueous layer neutralized or made alkaline and liberated anilines are separated and/or extracted with an organic solvent such as ether. The extract is dried and distilled to recover the fluoroaniline product.

EXAMPLE I

A 300 cc monel rocking autoclave was chilled to ~−20° to −40° C. under a nitrogen purge and charged with 15.72 g (0.1 mole) m-methoxynitrobenzene and 4.65 g (0.15 g-atm) red phosphorus. After the reaction chamber had cooled sufficiently (−20° to −40° C.) approximately 60 g (3.0 mole) anhydrous hydrogen fluoride was added. The reactor was sealed and heated to 150° C. developing a pressure of about 625 p.s.i.a., for 6 hours, then allowed to cool.

The residual gases were vented and HF allowed to evaporate. The solids were added to 100 cc of water then neutralized with 54% $NH_4OH$ to a pH of 7.0. Solids were filtered and dried under vacuum to yield 8.1 gms. An ether extract of the water layer provided an additional 1.0 gms of solids after drying over $MgSO_4$, filtering, and removing the solvent via distillation under vacuum.

Analysis of the combined 9.1 gms was performed in a p-dioxane solution under the following vapor phase chromatography conditions: Column 5 feet × ¼ inch 15% 6-ring polyphenylether on Anakrom ABS at 185° C., flow 50 cc He/min. Individual components were trapped and analyzed by infrared spectroscopy and/or nuclear magentic resonance. Analysis showed 29.4 m mole 2-fluoro-5-methoxyaniline, 19.6 m mole 2-fluoro-5-hydroxyaniline, and 6.8 m mole m-methoxynitrobenzene.

EXAMPLE II

A 300 cc monel rocking autoclave was chilled to ~−20° to −40° C. under a nitrogen purge and charged with 13.9 g (0.1 mole) m-hydroxy-nitrobenzene and 4.65 g (0.15 g-atm.) red phosphorus. After the reactor had cooled sufficiently (−20° to −40° C.) approximately 60 g (3.0 mole) anhydrous hydrogen fluoride was added. The reactor was sealed and heated to 150° C., developing a pressure of about 415 p.s.i.a., for 6 hours, then allowed to cool. The residual gases were vented and HF allowed to evaporate. The solids were added to 100 cc of water then neutralized with 54% $NH_4OH$ to a pH of 7.0. Solids were filtered and dried under vacuum. An ether extract of the water layer provided additional solids after drying over MgSO, filtering, and removing the solvent via distillation under vacuum.

EXAMPLE III

A 300 cc monel rocking autoclave was chilled to −70° C. under a nitrogen purge and charged with 13.9 g (0.1 mole) m-hydroxynitrobenzene and 27.5 g (0.20 moles) phosphorous trichloride. After the reactor had cooled sufficiently approximately 29 g (3.45 mole) anhydrous hydrogen fluoride was added. The reactor was heated to 150° C., developing a pressure of about 1200 p.s.i.g., for 6 hours, then allowed to cool. The residual gases were vented and HF distilled off. The solids were added to 100 cc of water then neutralized with 50% NaOH to a pH of 7.0. An ether extract of the water layer provided (6.0 g) solids after drying over $MgSO_4$, filtering, and removing the solvent via distillation under vacuum.

V.P.C. analysis of the combined yield was performed as described in Example I. 19.2 m moles 2-fluoro-5-hydroxyaniline were produced.

EXAMPLE IV

A 300 ml monel rocking autoclave was charged with 0.1 mole (15.6 g) m-nitrophenol and 0.2 mole (52.4 g) triphenyl phosphine. 85 g (4.25 mole) anhydrous hydrogen fluoride was added at −70° C. The autoclave was sealed and heated 6 hours at 150° C., generating a pressure of 200 p.s.i.g., then allowed to cool. The residual gasses were vented and HF distilled off under vacuum. To the solids was added 100 cc water and 100 g of ice. The mixture was filtered to remove triphenyl phosphine oxide and the filtrate basified to pH 10.0 then re-acidified to pH 7.0 and extracted with ether. The ether extract guilded 7.5 g of solids after drying over $MgSO_4$ and stripping.

G.C. analysis gave the following results:

| | yield (%) | Corrected yield (%) | Conversion (%) |
|---|---|---|---|
| 5-hydroxy-2-fluoroaniline | 18.9 | 20.4 | |
| 3-aminophenol | 28.2 | 30.4 | |
| 3-nitrophenol | | | 92.6 |

What is claimed is:
1. 5-Substituted-2-fluoroanilines having the formula

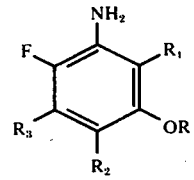

wherein R is selected from the group consisting of hydrogen and lower alkyl having 1–4 carbon atoms and $R_1$, $R_2$ and $R_3$ are each independently selected from the group consisting of hydrogen, halogen and lower alkyl having 1–4 carbons.

2. A 5-substituted-2-fluoroaniline as claimed in claim 1 wherein R is a lower alkyl having 1–4 carbon atoms.

3. A 5-substituted-2-fluoroaniline as claimed in claim 2 wherein R is $CH_3$.

* * * * *